United States Patent
Yagi

(10) Patent No.: US 11,767,288 B2
(45) Date of Patent: Sep. 26, 2023

(54) METHOD FOR PRODUCING AMINE THROUGH REDUCTION OF AMIDE

(71) Applicant: TAKASAGO INTERNATIONAL CORPORATION, Tokyo (JP)

(72) Inventor: Kenji Yagi, Atsugi (JP)

(73) Assignee: TAKASAGO INTERNATIONAL CORPORATION, Tokyo (JP)

(*) Notice: Subject to any disclaimer, the term of this patent is extended or adjusted under 35 U.S.C. 154(b) by 214 days.

(21) Appl. No.: 17/294,827

(22) PCT Filed: Dec. 10, 2019

(86) PCT No.: PCT/JP2019/048251
§ 371 (c)(1),
(2) Date: May 18, 2021

(87) PCT Pub. No.: WO2020/129749
PCT Pub. Date: Jun. 25, 2020

(65) Prior Publication Data
US 2021/0403411 A1    Dec. 30, 2021

(30) Foreign Application Priority Data
Dec. 19, 2018 (JP) .................... 2018-236872

(51) Int. Cl.
*C07C 209/50*    (2006.01)

(52) U.S. Cl.
CPC .................. *C07C 209/50* (2013.01)

(58) Field of Classification Search
None
See application file for complete search history.

(56) References Cited

U.S. PATENT DOCUMENTS

2009/0082568 A1    3/2009    Burkhardt

FOREIGN PATENT DOCUMENTS

CN    103435430 A    12/2013
JP    2010-539219 A    12/2010

OTHER PUBLICATIONS

Zhang et al. (Adv. Synthesis & Catalysis, 2013, 355 (14-15), 2775) (Year: 2013).*
Lubov Pasumansky et al., "Lithium Aminoborohydrides: Powerful, Selective, Air-Stable Reducing Agents", Organic Process Research & Development 2006, pp. 959-970, .vol. 10.
Christopher L. Bailey et al., "Controlled Reduction of Tertiary Amides to the Corresponding Alcohols, Aldehydes, or Amines Using Dialkylboranes and Aminoborohydride Reagents", The Journal of Organic Chemistry, 2016, pp. 3619-3628, .vol. 81.
Lan-Gui Xie et al., "Tertiary amine synthesis via reductive coupling of amides with Grignard reagents", Chemical Science, 2017, vol. 8, pp. 7492-7497 (6 pages total).
Office Action dated Apr. 20, 2023 from the Korean Patent Office in Application No. 10-2021-7014751.

* cited by examiner

*Primary Examiner* — Sudhakar Katakam
*Assistant Examiner* — Jennifer C Sawyer
(74) *Attorney, Agent, or Firm* — Sughrue Mion, PLLC

(57) ABSTRACT

The present invention provides a method for producing primary amines and secondary amines, the method being characterized by reducing a primary amide or a secondary amide in the presence of a reducing agent and an organic metal halide of a group-2 element.

4 Claims, No Drawings

METHOD FOR PRODUCING AMINE THROUGH REDUCTION OF AMIDE

CROSS REFERENCE TO RELATED APPLICATIONS

This application is a National Stage of International Application No. PCT/JP2019/048251 filed Dec. 10, 2019, claiming priority based on Japanese Patent Application No. 2018-236872 filed Dec. 19, 2018.

TECHNICAL FIELD

The present invention relates to a method for easily producing amines useful as fragrances or organic synthetic raw materials for pharmaceutical products in a high yield.

BACKGROUND ART

Several methods are known as methods for obtaining the corresponding amine from an amide using a reducing agent. Such methods include, for example, (A) a method of reduction with lithium aluminum hydride (LAH), (B) a method of reduction with a borane-based reagent, and (C) a method of reduction with a transition metal catalyst.

When the above method (A) is employed, there is a drawback that strict water control is required because the reactivity of LAH is extremely high. In addition, when the method (B) is employed, there is a concern that diborane, which is a toxic gas, is generated, and there is a drawback that it is difficult to operate on the actual production scale. Furthermore, when the method (C) is employed, there is a drawback that the production cost is high because an expensive metal catalyst is used.

In view of the above, as a method that avoids these drawbacks, a method that uses a borohydride-based reagent as a reducing agent has been reported (Non Patent Literature 1). This method is superior to the above-mentioned methods in that the reagent is easy to handle, does not produce by-products, and is relatively inexpensive.

However, although this method can obtain the corresponding amine or alcohol from a tertiary amide in a yield of 80% or more, the progress of reaction has not been confirmed with primary and secondary amides, and it cannot be applied to a wide range of substrates (Non Patent Literature 2).

CITATION LIST

Non Patent Literatures

Non Patent Literature 1: Organic Process Research & Development 2006, 10, 959-970.
Non Patent Literature 2: J. Org. Chem. 2016, 81, 3619-3628.

SUMMARY OF INVENTION

An object of the present invention is to provide a high-yield and economical method for producing an amine, which does not require the handling of reagents under strict water control.

The present inventors made earnest studies to achieve the above object, and have found as a result that when an organometallic halide of a Group 2 element and a borohydride compound or sodium bis(2-methoxyethoxy)aluminum hydride are used in combination, the reduction of primary amides and secondary amides proceeds, and the corresponding amines are obtained. Thus, the present invention has been completed.

Specifically, the present invention includes the following contents [1] to [7].

[1] A method for producing a primary amine and a secondary amine, comprising: reducing a primary amide or a secondary amide in the presence of an organometallic halide of a Group 2 element and a reducing agent.

[2] The production method according to [1] described above, wherein the primary amide or the secondary amide is an amide represented by the following general formula (1):

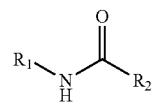

(1)

wherein $R_1$ and $R_2$ represent hydrogen, an alkyl group, a cycloalkyl group, an aryl group, an aralkyl group, a heterocyclic group, an alkenyl group, an alkynyl group, a cycloalkenyl group, an alkyloxy group, a cycloalkyloxy group, an aryloxy group, an aralkyloxy group, a hydroxyl group, an alkoxycarbonyl group, a cycloalkyloxycarbonyl group, an aryloxycarbonyl group, an aralkyloxycarbonyl group, an alkenyloxycarbonyl group, an alkynyloxycarbonyl group, or a cycloalkenyloxycarbonyl group, and these groups may have substituents, and in addition, $R_1$ and $R_2$ may form a ring, and the primary amine and the secondary amine are amines represented by the following general formula (2):

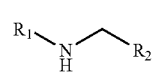

(2)

wherein $R_1$ and $R_2$ mean the same as above.

[3] The production method according to [1] or [2] described above, wherein the organometallic halide of the Group 2 element is a Grignard reagent.

[4] The production method according to [3] described above, wherein the amount of the Grignard reagent used is 1.0 to 5.0 equivalents with respect to the amide.

[5] The production method according to any one of [1] to [4] described above, wherein the reducing agent is a borohydride-based reagent or sodium bis(2-methoxyethoxy)aluminum hydride.

[6] The production method according to [5] described above, wherein the borohydride-based reagent is sodium borohydride, lithium borohydride, lithium dimethylamino borohydride, lithium pyrrolidino borohydride, or lithium morpholino borohydride.

[7] The production method according to [5] or [6] described above, wherein the amount of the reducing agent used is 1.0 to 5.0 equivalents with respect to the amide.

According to the present invention, reduction of primary amides and secondary amides proceeds using reagents that are easy to handle, and amines can be produced on the actual production scale.

DESCRIPTION OF EMBODIMENTS

The present invention is described in detail below.

Description is provided on $R_1$ and $R_2$ in the amide and amine represented by the general formulas (1) and (2) of the present invention.

The alkyl group may be linear or branched, and includes alkyl groups having 1 to 50 carbon atoms and preferably 1 to 20 carbon atoms, and includes, for example, a methyl group, an ethyl group, an n-propyl group, an isopropyl group, an n-butyl group, an isobutyl group, an s-butyl group, a tert-butyl group, an n-pentyl group, an n-hexyl group, an n-octyl group, an n-nonyl group, an n-decyl group, and the like.

The cycloalkyl group includes monocyclic, polycyclic, or condensed ring cycloalkyl groups having 3 to 30 carbon atoms, preferably 3 to 20 carbon atoms, and more preferably 3 to 10 carbon atoms, and includes, for example, a cyclopropyl group, a cyclopentyl group, a cyclohexyl group, a cyclooctyl group, a bicyclo[1.1.0]butyl group, a tricyclo[2.2.1.0]heptyl group, a bicyclo[3.2.1]octyl group, a bicyclo[2.2.2] octyl group, an adamantyl group (tricyclo[3.3.1.1]decanyl group), a bicyclo[4.3.2]undecanyl group, a tricyclo[5.3.1.1]dodecanyl group, and the like.

The aryl group includes monocyclic, polycyclic, or condensed ring aryl groups having 6 to 36 carbon atoms, preferably 6 to 18 carbon atoms, and more preferably 6 to 14 carbon atoms, and specifically includes, for example, a phenyl group, a naphthyl group, an anthryl group, a phenanthryl group, a biphenyl group, and the like.

The aralkyl group includes groups in which at least one hydrogen atom of the above-mentioned alkyl group is substituted with the above-mentioned aryl group, and includes, for example, aralkyl groups having 7 to 37 carbon atoms, preferably 7 to 20 carbon atoms, and more preferably 7 to 15 carbon atoms. The aralkyl group specifically includes, for example, a benzyl group, a 1-phenylethyl group, a 2-phenylethyl group, a 1-phenylpropyl group, a 3-naphthylpropyl group, and the like.

The heterocyclic group includes aliphatic heterocyclic groups and aromatic heterocyclic groups. The aliphatic heterocyclic groups include, for example, 3- to 8-membered, preferably 4- to 6-membered monocyclic aliphatic heterocyclic groups, and polycyclic or condensed ring aliphatic heterocyclic groups, having 2 to 14 carbon atoms and containing at least one, preferably 1 to 3 heteroatoms such as nitrogen atoms, oxygen atoms and/or sulfur atoms for example as heteroatoms. Specific examples of the aliphatic heterocyclic groups include an azetidyl group, an azetidino group, a pyrrolidyl group, a pyrrolidino group, a piperidinyl group, a piperidino group, a piperazinyl group, a piperazino group, a morpholinyl group, a morpholino group, a tetrahydrofuryl group, a tetrahydropyranyl group, a tetrahydrothiophenyl group, and the like.

The aromatic heterocyclic groups include, for example, 5- or 6-membered monocyclic heteroaryl groups and polycyclic or condensed ring heteroaryl groups having 2 to 15 carbon atoms and containing at least one, preferably 1 to 3 heteroatoms such as nitrogen atoms, oxygen atoms and/or sulfur atoms as heteroatoms Specific examples thereof include a furyl group, a thienyl group, a pyridyl group, a pyrimidyl group, a pyrazyl group, a pyridazyl group, a pyrazolyl group, an imidazolyl group, an oxazolyl group, a thiazolyl group, a benzofuryl group, a benzothienyl group, a quinolyl group, an isoquinolyl group, a quinoxalyl group, a phthalazyl group, a quinazolyl group, a naphthyridyl group, a cinnolyl group, a benzoimidazolyl group, a benzoxazolyl group, a benzothiazolyl group, an acridyl group, an acridinyl group, and the like.

The alkenyl group may be linear or branched, and includes, for example, alkenyl groups having 2 to 20 carbon atoms, preferably 2 to 15 carbon atoms, and more preferably 2 to 10 carbon atoms, and specific examples thereof include an ethenyl group, a propenyl group, a 1-butenyl group, a pentenyl group, a hexenyl group, a heptenyl group, an octenyl group, a nonenyl group, a decenyl group, and the like.

The alkynyl group may be linear or branched, and includes, for example, alkynyl groups having 2 to 20 carbon atoms, preferably 2 to 15 carbon atoms, and more preferably 2 to 10 carbon atoms, and specific examples thereof include, for example, an ethynyl group, a 1-propynyl group, a 2-propynyl group, a 1-butynyl group, a 3-butynyl group, a pentynyl group, a hexynyl group, and the like.

The cycloalkenyl group includes cycloalkenyl groups having 4 to 20 carbon atoms, preferably 4 to 15 carbon atoms, and more preferably 4 to 10 carbon atoms, and specific examples thereof include a cyclobutenyl group, a cyclopentenyl group, a cyclohexenyl group, a cycloheptenyl group, a cyclooctenyl group, and the like.

In addition, substituents that may be possessed by these alkyl group, cycloalkyl group, aryl group, alkenyl group, alkynyl group, aralkyl group, heterocyclic group, alkenyl group, alkynyl group, and cycloalkenyl group, as well as alkyloxy group, cycloalkyloxy group, aryloxy group, aralkyloxy group, hydroxyl group, alkoxycarbonyl group, cycloalkyloxycarbonyl group, aryloxycarbonyl group, aralkyloxycarbonyl group, alkenyloxycarbonyl group, alkynyloxycarbonyl group, and cycloalkenyloxycarbonyl group include the above-mentioned alkyl group, cycloalkyl group, aryl group, aralkyl group, alkenyl group, alkynyl group, cycloalkenyl, group and heterocyclic group, as well as a halogen atom described later, a silyl group described later, and a hydroxyl group that may be protected and is described later, an amino group, and the like.

The halogen atom as a substituent includes a fluorine atom, a chlorine atom, a bromine atom, and an iodine atom.

The silyl group as a substituent includes one in which three of the hydrogen atoms of the silyl group are substituted with the above-mentioned alkyl group, the above-mentioned aryl group, and the above-mentioned aralkyl group. The silyl group specifically includes a trimethylsilyl group, a triethylsilyl group, a t-butyldimethylsilyl group, a t-butyldiphenylsilyl group, a triphenylsilyl group, and the like.

The hydroxyl group that may be protected as a substituent includes unprotected hydroxyl groups and hydroxyl groups that may be protected by protective groups of general hydroxyl groups described in the literature (Protective Groups in Organic Synthesis Second Edition, JOHN WILEY & SONS, INC. 1991), and the protective groups include trisubstituted silyl groups such as a trimethylsilyl group, a tert-butyldimethylsilyl group, and a tert-butyldiphenylsilyl group, a benzyl group, and a methoxymethyl group, and the like.

When $R_1$ and $R_2$ are bonded to form a ring, $R_1$ and $R_2$ are divalent groups. Here, preferable groups include, for example, chain or branched or cyclic alkylene groups having 2 to 20 carbon atoms, more preferably 4 to 10 carbon atoms, chain or branched or cyclic alkenylene groups having 4 to 20 carbon atoms, more preferably 4 to 10 carbon atoms, arylene groups having 6 to 20 carbon atoms, more preferably 6 to 10 carbon atoms, and the like. These divalent groups may have substituents as described above.

Subsequently, the organometallic halide of the Group 2 element used in the present invention is described.

As the organometallic halide of the Group 2 element used in the production method of the present invention, an organic magnesium halide, a so-called Grignard reagent, is preferable.

The Grignard reagent specifically includes methylmagnesium chloride, ethylmagnesium chloride, isopropylmagnesium chloride, tert-butylmagnesium chloride, methylmagnesium bromide, ethylmagnesium bromide, isopropylmagnesium bromide, tert-butylmagnesium bromide, methylmagnesium iodide, ethylmagnesium iodide, isopropylmagnesium iodide, tert-butylmagnesium iodide, phenylmagnesium chloride, and the like, and it is preferable to use tert-butylmagnesium chloride. These Grignard reagents are usually used in an ether solution such as THF, and one kind or two or more kinds may be used in combination as appropriate.

The amount of the Grignard reagent used in the present invention is preferably 1.0 to 5.0 equivalents, particularly 1.2 to 1.5 equivalents, with respect to the amide, which is the raw material compound.

As the reducing agent used in the production method of the present invention, a borohydride-based reagent or sodium bis(2-methoxyethoxy)aluminum hydride is preferable, and one kind or two or more kinds of reducing agents may be used in combination as appropriate.

Specific borohydride-based reagents include sodium borohydride, lithium borohydride, lithium dimethylamino borohydride, lithium pyrrolidino borohydride, lithium morpholino borohydride, and the like, and it is preferable to use lithium dimethylamino borohydride.

The amount of the reducing agent used in the present invention is preferably 1.0 to 5.0 equivalents, particularly 1.2 to 3.0 equivalents, with respect to the amide which is the raw material compound.

The production method of the present invention is preferably carried out in the presence of a solvent. The solvent is not particularly limited as long as it is not involved in the reaction in the production method of the present invention, and specific examples of preferable solvents include, for example, aliphatic hydrocarbons such as pentane, hexane, heptane, octane, decane, dodecane, undecane, cyclohexane, and decalin, aromatic hydrocarbons such as benzene, toluene, xylene, mesitylene, p-cymene, and diisopropylbenzene, and ethers such as diethyl ether, diisopropyl ether, tert-butyl methyl ether, cyclopentyl methyl ether, dimethoxyethane, ethylene glycol diethyl ether, tetrahydrofuran (THF), and 1,4-dioxane, and the like. The amount of the solvent used is not particularly limited as long as the reaction in the production method of the present invention proceeds sufficiently, but is appropriately selected from the range of usually 1 to 100 times volume, preferably 5 to 20 times volume, with respect to the weight of the raw material amide.

In the production method of the present invention, the reaction temperature is not particularly limited, but is appropriately selected from the range of usually 30 to 180° C., preferably 100 to 150° C. The reaction time naturally differs depending on differences in reaction conditions, but is appropriately selected from the range of usually 30 minutes to 24 hours. In addition, it is desirable that the production method of the present invention is carried out in an inert gas atmosphere. The inert gas specifically includes nitrogen, argon, and the like.

The amine obtained by the production method of the present invention can be purified by distillation, column chromatography, and the like.

EXAMPLES

Hereinafter, the present invention is described in more detail with reference to Examples, but the present invention is not limited thereto.

[Measuring Equipment]

The following equipment was used to measure the physical properties of the compounds obtained in Examples.

GC/MS: GCMS-QP2010 SE (manufactured by Shimadzu Corporation)

Column: RTX-1 (length 30 m×inner diameter 0.25 mm, liquid phase film thickness 0.25 μm)

Gas chromatography purity: GC-4000 plus (manufactured by GL Science)

Column: Inert Cap1 (length 30 m×inner diameter 0.25 mm, liquid phase film thickness 0.25 μm)

Temperature condition: column 100° C.→10° C./min→300° C.

Injection port 250° C., detector 250° C. (FID)

(Example 1) Production of Amine Using Lithium Dimethylamino Borohydride

Each amide in an amount of 200 mg and a THF solution of tert-butylmagnesium chloride (1.0 M, 1.25 eq.) were added to a 50 mL autoclave, followed by stirring at room temperature for 30 minutes. Thereafter, a THF solution of lithium dimethylamino borohydride (1.0 M, 1.25 eq.) was added thereto, followed by stirring at a bath temperature of 120° C. for 5 hours. The reaction mixture was cooled to room temperature, and then quenched with methanol, and the product was confirmed by GC. The results are shown in Table 1 below.

Note that the selectivity is calculated by the following formula (the same applies hereinafter).

Selectivity (%)=(A)/(B)

A: Product GC area value
B: Product GC area value+GC area value other than the product (but excluding the GC area value of the reaction substrate)

TABLE 1

| Reaction Substrate | Product | Conversion Rate | Selectivity |
|---|---|---|---|
| Benzylbenzamide | N,N-Dibenzylamine | 100 | 92 |
| 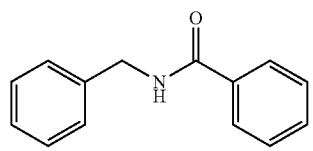 [SMILES: O=C(NCc1ccccc1)c1ccccc1] | 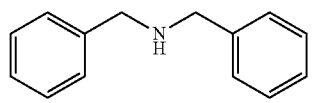 [SMILES: c1ccc(CNCc2ccccc2)cc1] | | |

TABLE 1-continued

| Reaction Substrate | Product | Conversion Rate | Selectivity |
|---|---|---|---|
| Benzylacetamide 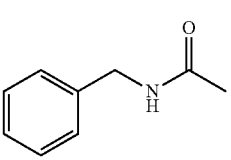 | Benzylethylamine 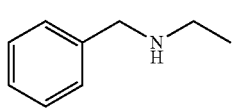 | 97 | 73 |
| Benzanilide 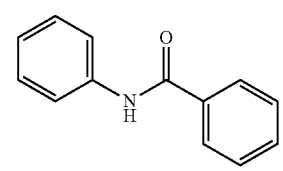 [SMILES: O=C(Nc1ccccc1)c1ccccc1] | N-Benzylaniline 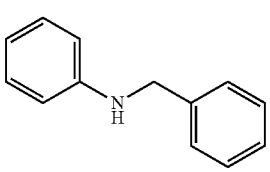 [SMILES: c1ccc(CNc2ccccc2)cc1] | 98 | 100 |
| Acetanilide 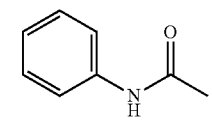 | N-Ethylaniline 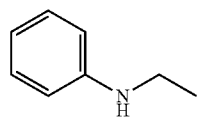 | 100 | 76 |
| Butylpropionamide 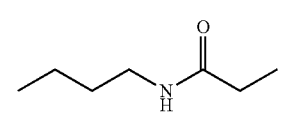 | Butylpropylamine 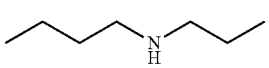 | 99 | 88 |
| Benzamide 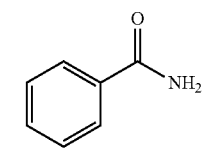 | Benzylamine 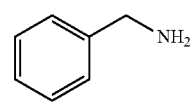 | 100 | 97 |
| Octanamide 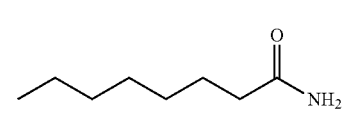 | Octylamine 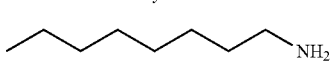 | 100 | 39 |
| Dimethylbenzamide 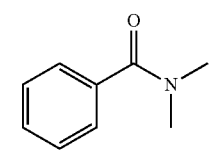 | N,N-Dimethylbenzylamine 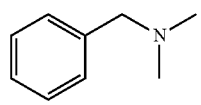 | 97 | 88 |

(Comparative Example 1) Reduction of Benzylbenzamide

Benzylbenzamide in an amount of 200 mg and 1.2 mL of THF were added to a 50 mL autoclave, followed by stirring at room temperature for 30 minutes. Thereafter, 1.2 mL (1.0 M, 1.25 eq.) of a THF solution of lithium dimethylamino borohydride was added thereto, followed by stirring at a bath temperature of 120° C. for 5 hours. The reaction mixture was cooled to room temperature, then quenched with methanol, and analyzed by GC. As a result, the conversion rate of benzylbenzamide was 3.7%.

(Example 2) Production of Amine Using Lithium Pyrrolidino Borohydride

Table 2 below shows the results of performing the same operations as in Example 1 using a THF solution of lithium pyrrolidino borohydride (1.0 M, 1.25 eq.) instead of lithium dimethylamino borohydride in Example 1.

TABLE 2

| Reaction Substrate | Product | Conversion Rate | Selectivity |
|---|---|---|---|
| Benzylbenzamide | N,N-Dibenzylamine | 100 | 97 |
| Benzylacetamide | Benzylethylamine | 95 | 79 |
| Benzanilide | N-Benzylaniline | 98 | 99 |
| Acetanilide | N-Ethylaniline | 100 | 62 |
| Butylpropionamide | Butylpropylamine | 100 | 93 |
| Benzamide | Benzylamine | 100 | 98 |
| Octanamide | Octylamine | 100 | 50 |

(Example 3) Production of Amine Using Lithium Morpholino Borohydride

Table 3 below shows the results of performing the same operations as in Example 1 using a THF solution of lithium morpholino borohydride (1.0 M, 1.25 eq.) instead of lithium dimethylamino borohydride in Example 1.

TABLE 3

| Reaction Substrate | Product | Conversion Rate | Selectivity |
|---|---|---|---|
| Benzylbenzamide | N,N-Dibenzylamine | 98 | 98 |
| Benzylacetamide | Benzylethylamine | 59 | 99 |
| Benzanilide | N-Benzylaniline | 96 | 89 |
| Acetanilide | N-Ethylaniline | 97 | 44 |
| Butylpropionamide | Butylpropylamine | 100 | 85 |
| Benzamide | Benzylamine | 100 | 88 |
| Octanamide | Octylamine | 100 | 79 |

(Example 4) Production of N,N-Dibenzylamine Using Lithium Borohydride

Benzylbenzamide in an amount of 200 mg and 1.2 mL of a THF solution of tert-butylmagnesium chloride (1.0 M, 1.25 eq.) were added to a 50 mL autoclave, followed by stirring at room temperature for 30 minutes. Then, 61.8 mg (3.0 eq.) of lithium borohydride was added thereto, followed by stirring at a bath temperature of 120° C. for 5 hours. The reaction mixture was cooled to room temperature, and then quenched with methanol, and the product was confirmed by GC. As a result, the target product was obtained with a conversion rate of 100% and selectivity of 99%.

(Example 5) Production of Amine Using Sodium Bis(2-Methoxyethoxy)Aluminum Hydride Table 4 below shows the results of performing the same operations as in Example 1 using a 70% toluene solution (1.25 eq.) of sodium bis(2-methoxyethoxy)aluminum hydride instead of lithium dimethylamino borohydride in Example 1.

TABLE 4

| Reaction Substrate | Product | Conversion Rate | Selectivity |
|---|---|---|---|
| Benzylbenzamide 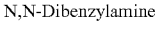 | N,N-Dibenzylamine 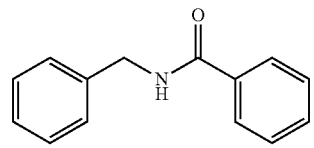 [SMILES: O=C(NCc1ccccc1)c1ccccc1] | 100 | 99 |
| Benzylacetamide 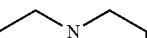 | Benzylethylamine 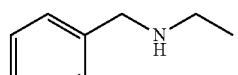 | 100 | 100 |
| Benzanilide 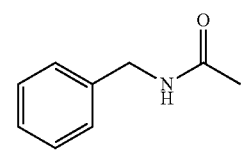 | N-Benzylaniline  | 97 | 100 |
| Acetanilide 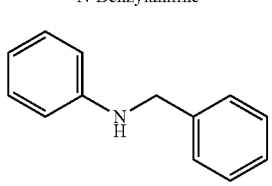 | N-Ethylaniline 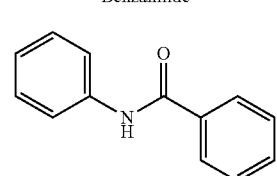 | 100 | 98 |
| Butylpropionamide 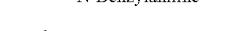 | Butylpropylamine 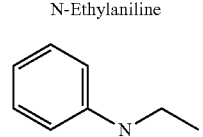 | 100 | 99 |
| Benzamide 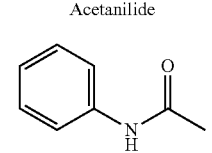 | Benzylamine 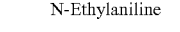 | 100 | 96 |
| Octanamide 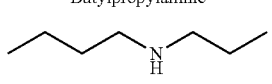 | Octylamine  | 100 | 94 |

INDUSTRIAL APPLICABILITY

According to the present invention, amines useful as fragrances or organic synthetic raw materials for pharmaceutical products and the like can be obtained in a high yield and extremely advantageously from the viewpoint of production economy, and thus the present invention can be expected to be widely utilized in the fields of cosmetics, pharmaceutical products, and the like.

What is claimed is:

1. A method for producing a primary amine and a secondary amine, comprising: reducing a primary amide or a secondary amide in the presence of an organometallic halide of a Group 2 element and a reducing agent, wherein
the primary amide or the secondary amide is an amide represented by the following formula (1):

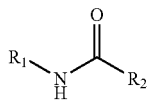

(1)

wherein $R_1$ and $R_2$ each independently represent hydrogen, an alkyl group, a cycloalkyl group, an aryl group, an aralkyl group, a heterocyclic group, an alkenyl group, an alkynyl group, a cycloalkenyl group, an alkyloxy group, a cycloalkyloxy group, an aryloxy group, an aralkyloxy group, a hydroxyl group, an alkoxycarbonyl group, a cycloalkyloxycarbonyl group, an aryloxycarbonyl group, an aralkyloxycarbonyl group, an alkenyloxycarbonyl group, an alkynyloxycarbonyl group, or a cycloalkenyloxycarbonyl group, each of which optionally have a substituent; and $R_1$ and $R_2$ together may form a ring, and the primary amine and the secondary amine are amines represented by the following formula (2):

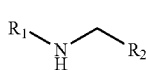

(2)

wherein $R_1$ and $R_2$ mean the same as above, and
the organometallic halide of the Group 2 element is a Grignard reagent, and
the reducing agent is a borohydride-based reagent or sodium bis(2-methoxyethoxy)aluminum hydride.

2. The production method according to claim 1, wherein the amount of the Grignard reagent is 1.0 to 5.0 equivalents with respect to the amide.

3. The production method according to claim 1, wherein the borohydride-based reagent is sodium borohydride, lithium borohydride, lithium dimethylamino borohydride, lithium pyrrolidino borohydride, or lithium morpholino borohydride.

4. The production method according to claim 1, wherein the amount of the reducing agent is 1.0 to 5.0 equivalents with respect to the amide.

\* \* \* \* \*